United States Patent
Gruenwald et al.

(10) Patent No.: US 10,121,244 B2
(45) Date of Patent: Nov. 6, 2018

(54) TRANSFORMATION DETERMINATION DEVICE AND METHOD FOR DETERMINING A TRANSFORMATION FOR IMAGE REGISTRATION

(71) Applicant: Siemens Healthcare GmbH, Erlangen (DE)

(72) Inventors: Oxana Gruenwald, Forchheim (DE); Bernd Schreiber, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 48 days.

(21) Appl. No.: 15/246,673

(22) Filed: Aug. 25, 2016

(65) Prior Publication Data

US 2017/0076447 A1    Mar. 16, 2017

(30) Foreign Application Priority Data

Sep. 10, 2015   (DE) .................. 10 2015 217 317

(51) Int. Cl.
  *G06K 9/00*   (2006.01)
  *G06T 7/00*   (2017.01)
  (Continued)

(52) U.S. Cl.
  CPC ............ *G06T 7/0012* (2013.01); *A61B 5/055* (2013.01); *A61B 6/4441* (2013.01); *A61B 6/481* (2013.01);
  (Continued)

(58) Field of Classification Search
  CPC ....... A61B 5/055; A61B 6/4441; A61B 6/481; A61B 6/504; A61B 6/5205; A61B 6/5217;
  (Continued)

(56) References Cited

U.S. PATENT DOCUMENTS

2008/0037845 A1* 2/2008 Deuerling-Zheng ..... G06T 7/32
                                                   382/130
2008/0049994 A1* 2/2008 Rognin ..................... G06T 7/35
                                                   382/128

(Continued)

OTHER PUBLICATIONS

Image registration for DSA quality enhancement Thorsten M. Buzug, Jürgen Weese; Thorsten M. Buzug et al.; Image registration for DSA quality enhancement; Journal of Computerized Medical Imaging and Graphics; vol. 22, Issue 2, pp. 103-113 (Mar. 1998); 1998.

(Continued)

*Primary Examiner* — Bhavesh Mehta
*Assistant Examiner* — Ian Lemieux
(74) *Attorney, Agent, or Firm* — Harness, Dickey & Pierce, P.L.C.

(57) ABSTRACT

A method is for determining a transformation for image registration of a first image relative to a second image. The method includes ascertaining a test series of test elements including a test transformation and a test value, the ascertaining including ascertaining the test transformation based on a sequence of test transformations and/or based on previously ascertained test elements, transforming the first image via the ascertained test transformation, ascertaining a difference image, and ascertaining the test value of the test element based on the difference image such that the test value is a measure for an extension of a frequency distribution of values of pixels of the difference image in a direction of pixel value increase. It further includes determining a minimum test value based on test values encompassed by the test elements and determining the transformation which is the test transformation of a test element including the minimum test value.

29 Claims, 8 Drawing Sheets

(51) Int. Cl.

| | | |
|---|---|---|
| *A61B 5/055* | (2006.01) | |
| *A61B 6/00* | (2006.01) | |
| *G06K 9/52* | (2006.01) | |
| *G06K 9/62* | (2006.01) | |
| *G06T 3/20* | (2006.01) | |
| *G06T 3/60* | (2006.01) | |
| *G06T 3/00* | (2006.01) | |
| *G06T 7/30* | (2017.01) | |

(52) U.S. Cl.
CPC ............ *A61B 6/504* (2013.01); *A61B 6/5205* (2013.01); *A61B 6/5217* (2013.01); *G06K 9/52* (2013.01); *G06K 9/6203* (2013.01); *G06K 9/6215* (2013.01); *G06T 3/0068* (2013.01); *G06T 3/20* (2013.01); *G06T 3/60* (2013.01); *G06T 7/30* (2017.01); *G06K 2209/05* (2013.01)

(58) Field of Classification Search
CPC .... G06K 2209/05; G06K 9/52; G06K 9/6203; G06K 9/6215; G06T 3/0068; G06T 3/20; G06T 3/60; G06T 7/0012; G06T 7/30
See application file for complete search history.

(56) References Cited

U.S. PATENT DOCUMENTS

2009/0046951 A1* 2/2009 Paragios ................. G06K 9/32
  382/294
2015/0030228 A1 1/2015 Kohler

OTHER PUBLICATIONS

German Office Action dated Apr. 11, 2017.
Deuerling-Zheng Y. et al.: "Motion compensation in digital subtraction angiography using graphics hardware", in: Computerized Medical Imaging and Graphics, vol. 30, pp. 279-289, 2006.
German Office Action dated Jun. 13, 2016.

* cited by examiner

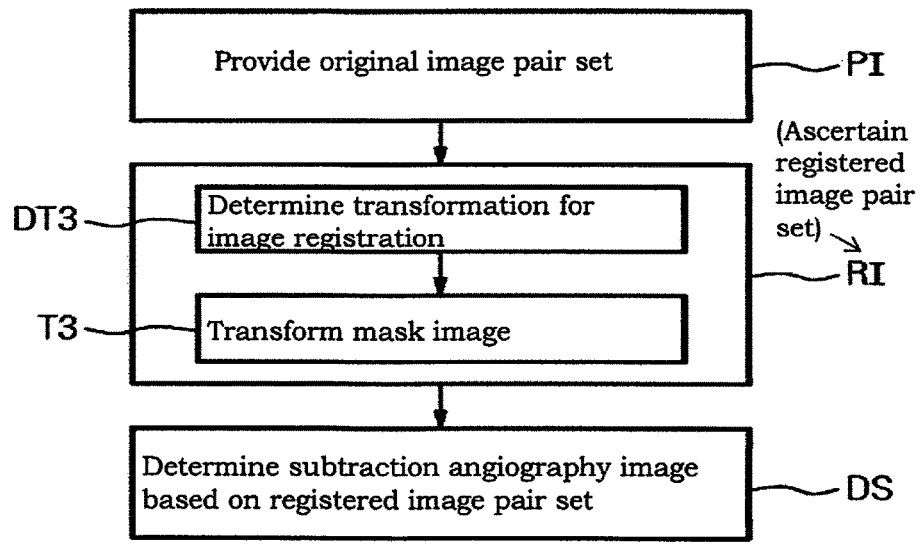
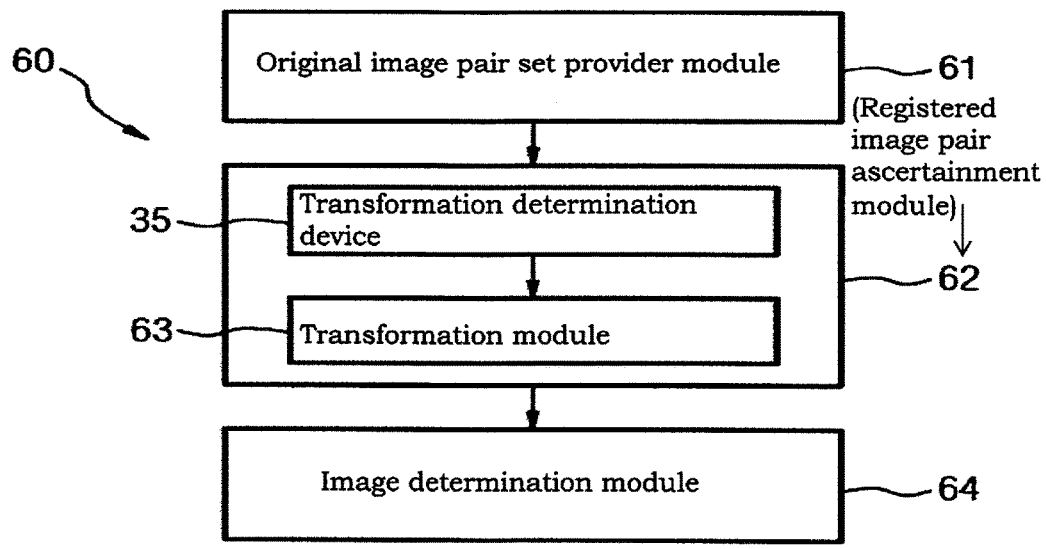

FIG 6
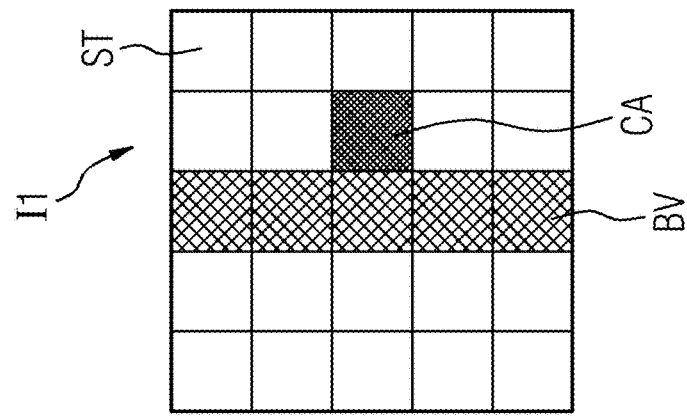
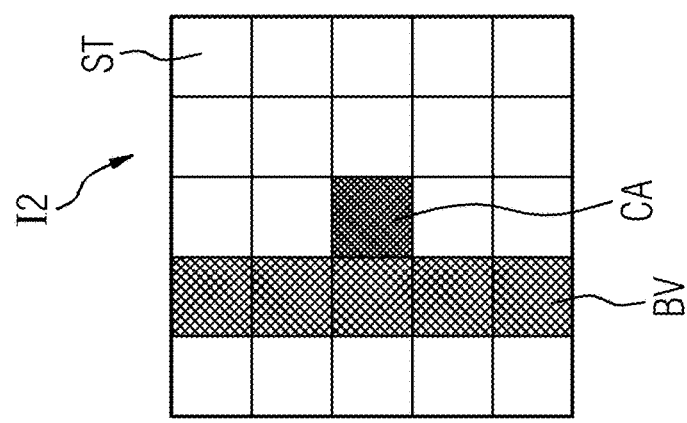
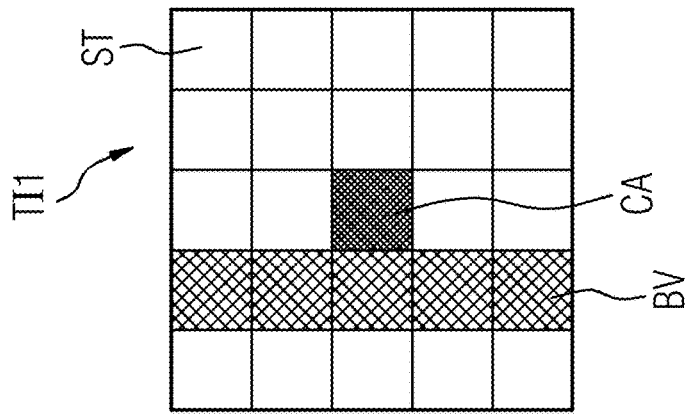

TRANSFORMATION DETERMINATION DEVICE AND METHOD FOR DETERMINING A TRANSFORMATION FOR IMAGE REGISTRATION

PRIORITY STATEMENT

The present application hereby claims priority under 35 U.S.C. § 119 to German patent application number DE 102015217317.8 filed Sep. 10, 2015, the entire contents of which are hereby incorporated herein by reference.

FIELD

At least one embodiment of the invention generally relates to a method for determining a transformation for image registration of a first image relative to a second image. At least one embodiment of the invention further generally relates to a method for determining a subtraction angiography image, to a transformation determination device, to an image determination device, to an imaging apparatus, to a computer program product, and/or to a computer-readable medium.

BACKGROUND

In digital image processing, an image registration serves in particular to establish a correlation between a plurality of images of a region of interest that is to be imaged in such a way that when the plurality of images are combined pixel by pixel, those pixels are combined with one another which relate to the same part of the region to be imaged. During the image registration of a first image relative to a second image, for example, the first image can be transformed in such a way that those pixels which relate to the same part of the region to be imaged are located at the same position in the first image and in the second image.

In digital subtraction angiography (DSA), an original image pair set containing one or more original image pairs is typically acquired of the same region of a patient that is to be imaged, wherein each original image pair of the original image pair set has a contrast agent image and a mask image. The contrast agent image is typically acquired while a contrast agent is present in the region to be imaged. The mask image is typically acquired while no or an extremely small amount of contrast agent is present in the region to be imaged. Via a pixel-by-pixel subtraction of the mask image from the contrast agent image it is possible for a structure of the region to be imaged in which contrast agent is present to be visualized more clearly with respect to an environment of the structure that is free of contrast agent.

In three-dimensional digital subtraction angiography (3D-DSA), a 3D subtraction angiography image is determined based on an original image pair set containing a plurality of original image pairs, wherein each original image pair of the original image pair set has a mask image and a contrast agent image. In particular, the 3D subtraction angiography image can be determined via a technique known as dual volume reconstruction. Using said technique, a 3D mask image dataset can be determined based on the mask images and/or transformed mask images and a 3D contrast agent image dataset can be determined based on the contrast agent images. The 3D subtraction angiography image can be determined through combination of the 3D mask image dataset with the 3D contrast agent image dataset.

The mask image and the contrast agent image are acquired at different points in time. In the time interval lying therebetween, the position of the region to be imaged can change. Possible reasons for this are e.g. a movement of the patient, mechanical vibrations of the raw data acquisition apparatus and/or of the C-arm, fluctuations in an X-ray beam focus or pulsating blood vessels. This can lead to a misregistration of the mask image relative to the contrast agent image such that in a pixel-by-pixel combination, in particular a subtraction, of the mask image and the contrast agent image, those pixels which relate to the same part of the region to be imaged are not combined with one another. The misregistration can result in the quality of a subtraction angiography image which is determined based on the mask image and the contrast agent image being degraded due to artifacts, and consequently can lead to misdiagnoses. Typically, the degradation in image quality is particularly severe when metal, e.g. a coil inserted into an aneurysm, is present in the region to be imaged. In 3D-DSA, a type of artifact known as an eggshell artifact can be produced in this way. In particular in the case of eggshell artifacts it is often difficult to decide to what extent a circulation of blood in the aneurysm is suppressed due to the coil.

SUMMARY

The inventors recognize that the image registration of the mask image relative to the contrast agent image takes on huge importance. An example of a known image registration method is the flexible pixel shift algorithm, which is implemented e.g. in the 3D reconstruction software of the syngo X workplace product.

In at least one embodiment of the invention, an image registration of a first image relative to a second image is improved.

At least one embodiment is directed to a method; at least one embodiment is directed to a transformation determination device; at least one embodiment is directed to an image determination device; at least one embodiment is directed to an imaging apparatus; at least one embodiment is directed to a computer program product; and at least one embodiment is directed to a computer-readable medium.

In the method according to at least one embodiment of the invention for determining a transformation for image registration of a first image relative to a second image, a test series of test elements is ascertained, wherein each test element comprises a test transformation and a test value, wherein each test element of the test series is ascertained by at least the following:

ascertaining the test transformation of the test element based on a predetermined sequence of test transformations and/or based on one or more previously ascertained test elements, transforming the first image by way of the ascertained test transformation, ascertaining a difference image based on the transformed first image and the second image, ascertaining the test value of the test element based on the difference image in such a way that the test value is a measure for an extension of a frequency distribution of values of pixels of the difference image in the direction in which the values of the pixels increase.

In an embodiment of the inventive method for determining a subtraction angiography image based on an original image pair set containing one or more original image pairs, wherein each original image pair of the original image pair set has a mask image and a contrast agent image, an original image pair set is provided. A registered image pair set containing one or more registered image pairs is ascertained by performing at least the following for each original image pair of the original image pair set:

determining a transformation for image registration by way of an embodiment of the inventive method for determining a transformation for image registration of a first image relative to a second image, wherein the first image is the mask image of the original image pair and the second image is the contrast agent image of the original image pair, and transforming the mask image by way of the determined transformation, wherein the transformed mask image and the contrast agent image form a registered image pair of the registered image pair set.

An embodiment of the inventive transformation determination device is embodied for determining a transformation for image registration of a first image relative to a second image and has a test series ascertainment module, a minimum test value determination module and a transformation determination module. The test series ascertainment module is embodied for ascertaining a test series of test elements, wherein each test element comprises a test transformation and a test value. The test series ascertainment module is embodied for performing at least the following for each test element of the test series:

ascertaining the test transformation of the test element based on a predetermined sequence of test transformations and/or based on one or more previously ascertained test elements, transforming the first image via the ascertained test transformation, ascertaining a difference image based on the transformed first image and the second image, and ascertaining the test value of the test element based on the difference image in such a way that the test value is a measure for an extension of a frequency distribution of values of pixels of the difference image in the direction in which the values of the pixels increase.

According to an aspect of an embodiment of the invention, the inventive transformation determination device is embodied for performing an embodiment of the inventive method for determining a transformation for image registration. In particular, the ascertainment of the test series of test elements via the test series ascertainment module, the determining of the minimum test value via the minimum test value determination module and the determining of the transformation which is the test transformation of a test element comprising the minimum test value can be performed via the transformation determination module.

The image determination device according to an embodiment of the invention is embodied for determining a subtraction angiography image based on an original image pair set containing one or more original image pairs, wherein each original image pair of the original image pair set has a mask image and a contrast agent image. An embodiment of the inventive image determination device has an original image pair set provider module, a registered image pair ascertainment module and an image determination module.

The original image pair set provider module is embodied for providing the original image pair set. The registered image pair ascertainment module has an embodiment of the inventive transformation determination device and a transformation module. The registered image pair ascertainment module is embodied for ascertaining a registered image pair set containing one or more registered image pairs by performing at least the following for each original image pair of the original image pair set:

determining a transformation via the inventive transformation determination device, wherein the first image is the mask image of the original image pair and the second image is the contrast agent image of the original image pair, and transforming the mask image by way of the determined transformation via the transformation module, wherein the transformed mask image and the contrast agent image form a registered image pair of the registered image pair set.

An embodiment of an inventive determination device is to be understood as a device that is chosen from the group including an embodiment of an inventive transformation determination device and an embodiment of an inventive image determination device. An embodiment of the inventive imaging apparatus includes an embodiment of the inventive determination device.

An embodiment variant of the invention provides that the imaging apparatus is a medical imaging apparatus and/or that the imaging apparatus has a raw data acquisition apparatus and/or a patient support apparatus. The raw data acquisition apparatus is embodied for acquiring a raw data set. In particular, the raw data acquisition apparatus can comprise a radiation source and a detector. In a C-arm X-ray machine, the radiation source can be an X-ray source and the detector an X-ray detector. In a magnetic resonance tomography system, the radiation source can be a radiofrequency antenna and the detector the same radiofrequency antenna or a further radiofrequency antenna. The patient support apparatus is embodied for supporting and positioning a patient.

An embodiment variant of the invention provides that an embodiment of the inventive determination device and/or one or more components of the inventive determination device are realized at least in part in the form of software on a processor system. In particular, the test series ascertainment module, the minimum test value determination module, the transformation determination module, the original image pair set provider module, the registered image pair ascertainment module, the transformation module and the image determination module in each case form a component of an embodiment of the inventive determination device. An embodiment variant of the invention provides that an embodiment of the inventive determination device and/or one or more components of an embodiment of the inventive determination device are realized at least in part in the form of software-assisted hardware, for example FPGAs or the like.

An embodiment variant of the invention provides that the original image pair set is provided with the aid of a data transfer from the original image pair set provider module to the registered image pair ascertainment module. An embodiment variant of the invention provides that the original image pair set provider module has at least one access module for accessing a memory area, e.g. of a computer and/or control device of an imaging apparatus, in which the original image pair set is stored. The data transfer can be accomplished e.g. by way of a suitable interface. An embodiment variant of the invention provides that interfaces for data transfer to and/or from components of the inventive determination device are realized at least in part in the form of software. In particular, the interfaces can have at least one access module for accessing suitable memory areas in which data can be suitably buffered, retrieved and updated. The interfaces can also be embodied as hardware-based interfaces which are controlled via suitable software.

A largely software-based implementation has the advantage that existing control devices already used in the prior art can also be easily upgraded via a software update in order to operate in the inventive manner. In this respect an embodiment relates to a corresponding computer program product having a computer program which can be loaded into a memory device of a computer, wherein an embodiment of an inventive method is performed by way of the computer program when the computer program is executed in the control device. As well as the computer program, such a computer program product can comprise additional software components, e.g. documentation, and/or hardware components, e.g. a hardware key (dongle, etc.) to enable use of the software.

In an embodiment, in order to transport the computer program to the control device and/or to store the computer program on or in the control device, a computer-readable medium can be used, for example a memory stick, a hard disk or some other transportable or permanently installed data medium on which a computer program which can be loaded into a memory device of a computer is stored, wherein an embodiment of an inventive method is performed by way of the computer program when the computer program is executed on the computer. An embodiment variant of the invention provides that the control device has a processor system. The processor system can be formed e.g. by one or more cooperating microprocessors.

According to an aspect of the invention, the imaging apparatus is chosen from the group including a C-arm X-ray machine, a computed tomography device, a single photon emission computed tomography device (SPECT device), a positron emission tomography device (PET device), a magnetic resonance tomography device, and combinations thereof. In particular, the imaging apparatus can comprise an X-ray machine, an ultrasound device and similar. The imaging apparatus can furthermore be a combination of a plurality of imaging and/or irradiation modalities. In this case an irradiation modality can comprise for example an irradiation device for radiation therapy.

BRIEF DESCRIPTION OF THE DRAWINGS

The invention is explained in more detail once again hereinbelow with the aid of example embodiments and with reference to the attached figures. The illustration in the figures is schematic and greatly simplified as well as not necessarily being true to scale.

In the figures:

FIG. 3 is a flowchart of a method for determining a subtraction angiography image according to a third embodiment variant of the invention, FIG. 4 is an illustration of an image determination device according to a fourth embodiment variant of the invention, FIG. 6 shows, in a greatly simplified illustration, a first image, a second image and a transformed first image according to a sixth embodiment variant of the invention.

DETAILED DESCRIPTION OF THE EXAMPLE EMBODIMENTS

Figure 1:
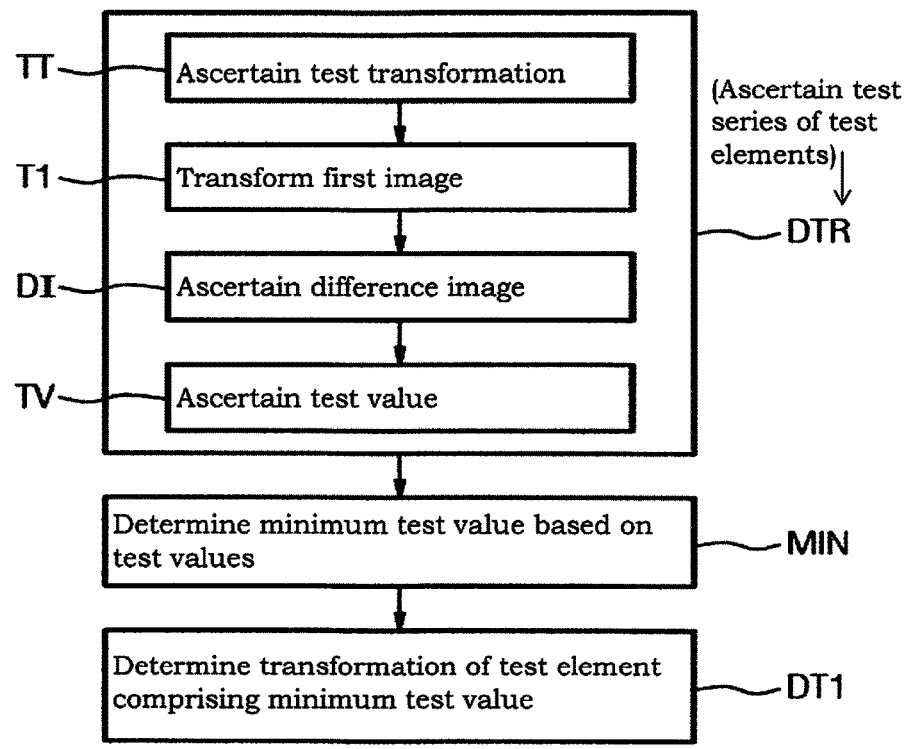
FIG. 1 is a flowchart of a method for determining a transformation for image registration according to a first embodiment variant of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the method according to at least one embodiment of the invention for determining a transformation for image registration of a first image relative to a second image, a test series of test elements is ascertained, wherein each test element comprises a test transformation and a test value, wherein each test element of the test series is ascertained by at least the following:

ascertaining the test transformation of the test element based on a predetermined sequence of test transformations and/or based on one or more previously ascertained test elements, transforming the first image via the ascertained test transformation, ascertaining a difference image based on the transformed first image and the second image, ascertaining the test value of the test element based on the difference image in such a way that the test value is a measure for an extension of a frequency distribution of values of pixels of the difference image in the direction in which the values of the pixels increase.

A minimum test value is determined based on the test values encompassed by the test elements of the test series. The transformation which is the test transformation of a test element comprising the minimum test value is determined.

The test value is a measure for the extension of a frequency distribution of values of pixels in the direction in which the values of the pixels increase in particular when the test value is dependent on the values of the pixels in such a way that a change in the values of the pixels that corresponds to a shifting and/or stretching of the frequency distribution in the direction in which the values of the pixels increase leads to an increase in the test value.

The inventors recognize that an optimal transformation for image registration can be determined by testing different test transformations in relation to their suitability for image registration and rating them with a test value. The inventors propose that the test value be ascertained in such a way that a test transformation which results in the difference image having one or more pixels with comparatively larger values is penalized more heavily, in particular is rated as less suitable for the image registration. The test value can be ascertained in particular based on the values of the pixels of the difference image. In this case the one pixel or the plurality of pixels having the greatest, in other words maximum, values can be weighted more heavily compared to pixels having smaller values.

An embodiment variant of the invention provides that test transformations which are less suitable for image registration are assigned larger test values. The optimal transformation for image registration can therefore be determined by identifying, among the test transformations of the test series, the test transformation having the minimum test value. The method according to the invention can in this regard be described as a "Minimum of Maximum" (MoM) method.

An embodiment variant of the invention provides that the first image and the second image are acquired with the aid of a radiation dose penetrating the region to be imaged and that the values of the pixels of the first image and the values of the pixels of the second image are dependent on an absorption of the radiation in such a way that a stronger absorption of the radiation in a part of the region to be imaged to which a given pixel relates results in a smaller value of the given pixel. The values of the pixels can be in particular grayscale values and/or brightness values. The values of the pixels can be in particular absorption values and/or intensity values.

An embodiment variant of the invention provides that the difference image is ascertained by subtracting the transformed first image from the second image one pixel at a time. Typically, the difference image has a pixel with a comparatively large value when a small value of a pixel of the transformed first image is subtracted from a large value of a pixel of the second image. This case occurs in particular when, on account of the misregistration, a pixel relating to a part of the region to be imaged exhibiting stronger absorption is subtracted from a pixel relating to a part of the region to be imaged exhibiting weaker absorption. A part of the region to be imaged exhibiting stronger absorption can comprise e.g. a part of a blood vessel and/or of an aneurysm and/or of a metal object, in particular a coil inserted into an aneurysm. A part of the region to be imaged exhibiting weaker absorption can comprise e.g. a part of a tissue.

By way of the method according to at least one embodiment of the invention, it is possible in particular to determine a transformation for image registration in such a way that, during the ascertainment of the difference image, pixels of the second image having in each case a large value or exhibiting strong absorption have subtracted from them pixels of the first image, likewise having in each case a large value or exhibiting weak absorption. This results in a reduction of the extension of the frequency distribution of values of pixels of the difference image in the direction in which the values of the pixels increase. The test value associated with said transformation is therefore comparatively small, with the result that the transformation can be determined from the set of test transformations of the test series via a minimum search relating to the test value.

According to an aspect of at least one embodiment of the invention, the test value is ascertained based on a pixel group of the difference image, wherein a pixel position condition relating to a position of the pixel and/or a pixel value condition relating to a value of the pixel is met for each pixel of the pixel group.

An embodiment variant of the invention provides that the pixel group comprises the pixels of the difference image for which a position condition relating to a position of the respective pixel and/or a pixel value condition relating to a value of the respective pixel is met.

The frequency distribution can relate to the entire difference image and/or to a pixel group of the difference image, wherein a pixel position condition relating to a position of the pixel and/or a pixel value condition relating to a value of the pixel is met for each pixel of the pixel group. An embodiment variant of the invention provides that a pixel group of pixels of the difference image is ascertained, wherein a pixel position condition relating to a position of the pixel and/or a pixel value condition relating to a value of the pixel is met for each pixel of the pixel group. An embodiment variant of the invention provides that the test value of the test element is ascertained and/or calculated based on the values of the pixels of the pixel group and/or that the test value is a measure for the values of the pixels of the pixel group. Ascertaining the test value in such a way that a plurality of values of pixels contribute in each case to the test value enables the error susceptibility of the method in relation to outliers to be reduced.

According to an aspect of an embodiment of the invention, the test value is a parameter of the pixel group and/or of the difference image and/or the test value is ascertained based on a parameter of the pixel group and/or of the difference image, wherein the parameter is chosen from the group which includes a maximum of the values of the pixels, a sum of the values of the pixels and a location parameter of a frequency distribution of the values of the pixels. An embodiment variant of the invention provides that the test value is ascertained based on a plurality of parameters of the pixel group and/or of the difference image, wherein each of the parameters of the plurality of parameters is chosen from the group which includes a maximum of the values of the pixels, a sum of the values of the pixels and a location parameter of a frequency distribution of the values of the pixels. An embodiment variant of the invention provides that the test value is ascertained based on the parameter and/or based on the plurality of parameters, wherein the test value is dependent in a monotonically increasing manner on the parameter or on each of the parameters of the plurality of parameters. An embodiment variant of the invention provides that the test value is the maximum of the values of the pixels of the pixel group and/or of the difference image. An embodiment variant of the invention provides that the test value is the sum of the values of the pixels of the pixel group. According to an aspect of the invention, the location parameter is chosen from the group which includes a mean value, a mode and a quantile.

According to an aspect of an embodiment of the invention, the pixel position condition for a given pixel of the difference image is met when the position of the given pixel is located in a region of interest (RoI). With the aid of the pixel position condition it is possible to restrict the pixel group in relation to the positions of the pixels of the pixel group. Preferably, the region of interest is determined in such a way that the part of the region to be imaged affected by the pixels of the pixel group is particularly sensitive in relation to a misregistration. This is typically the case when a section having large pixel values is contiguous with a section having small pixel values in the region of interest. In such a case even a slight misregistration corresponding e.g. to a translation by one pixel results in large pixel values in the difference image and consequently a severe degradation in quality, e.g. of the DSA image, due to artifacts.

An embodiment variant of the invention provides that a subregion is ascertained in the first image and/or in the second image, wherein the pixels of the subregion have smaller values relative to an environment of the subregion and/or wherein the subregion comprises both pixels having large values and pixels having small values and/or wherein the values of the pixels of the subregion form a gradient whose gradient magnitude exceeds a gradient magnitude threshold value. An embodiment variant of the invention provides that the region of interest comprises the subregion and/or the environment of the subregion.

According to an aspect of an embodiment of the invention, the pixel value condition for a given pixel of the difference image is met when the value of the given pixel exceeds a pixel threshold value. With the aid of the pixel position condition and/or of the pixel value condition, pixels can be selected for the pixel group from regions that are particularly relevant for the image registration and/or pixels can be excluded from the pixel group that are less relevant for the image registration. In this way it is possible to achieve a reduction in the computational overhead and in the error susceptibility of the method.

According to an aspect of an embodiment of the invention, the test transformation comprises a translation and/or a rotation. An embodiment variant of the invention provides that the test transformation alternatively or additionally comprises a further image operation, e.g. a local or a global image operation. An embodiment variant of the invention provides that the test transformation is a test transformation in the plane of the first image and/or that the translation is a translation in the plane of the first image and/or that the rotation is a rotation in the plane of the first image.

An embodiment variant of the invention provides that a sequence of test transformations is predetermined. The predetermined sequence of test transformations can include one test transformation or a plurality of test transformations. Starting with a first test transformation of the predetermined sequence of test transformations, a first test value is ascertained. The first test transformation of the predetermined sequence and the first test value form the first test element of the test series. Next, a further test value can be ascertained via a further test transformation of the predetermined sequence of test transformations. The further test transformation of the predetermined sequence and the further test value form a further test element of the test series. This step can be repeated e.g. for one or more or all test transformations of the predetermined sequence of test transformations.

The test transformation of the test element can be ascertained in particular based on a predetermined sequence of test transformations. For example, with the exception of the first test transformation of the predetermined sequence, each test transformation of the predetermined sequence of test transformations can differ compared to the respective preceding test transformation by a translation by one pixel in the same or in a different direction. For example, the predetermined sequence of test transformations can comprise all translations up to a given number of pixels, e.g. up to five pixels.

According to an aspect of an embodiment of the invention, the test transformation is ascertained via a search algorithm. An embodiment variant of the invention provides that the test transformation of the test element is ascertained via a search algorithm based on one or more previously ascertained test elements. The search algorithm can be a minimum search algorithm and/or e.g. a downhill simplex algorithm.

According to an aspect of an embodiment of the invention, the test value is compared with a test threshold value, wherein the ascertainment of the test series is not continued further if the test value falls below the test threshold value. An embodiment variant of the invention provides that the test value is compared with a test threshold value, wherein the ascertainment of the test series is terminated if the test value falls below the test threshold value.

In an embodiment of the inventive method for determining a subtraction angiography image based on an original image pair set containing one or more original image pairs, wherein each original image pair of the original image pair set has a mask image and a contrast agent image, an original image pair set is provided. A registered image pair set containing one or more registered image pairs is ascertained by performing at least the following for each original image pair of the original image pair set:

determining a transformation for image registration by way of an embodiment of the inventive method for determining a transformation for image registration of a first image relative to a second image, wherein the first image is the mask image of the original image pair and the second image is the contrast agent image of the original image pair, and transforming the mask image via the determined transformation, wherein the transformed mask image and the contrast agent image form a registered image pair of the registered image pair set.

In an embodiment, the subtraction angiography image is determined based on the registered image pair set.

An embodiment variant of the invention provides that the first image is two-dimensional (2D) and/or that the second image is two-dimensional (2D) and/or that the image registration is a 2D-2D image registration. An embodiment variant of the invention provides that the subtraction angiography image is a 2D subtraction angiography image or that the subtraction angiography image is a 3D subtraction angiography image. The method according to an embodiment of the invention can furthermore be advantageously employed also in the case of a method for determining so-called 2D roadmap images and/or fluoroscopic images.

By a strong and/or a stronger absorption may be understood in particular an absorption by a blood vessel filled with contrast agent and/or an absorption by a metal object. By a weak and/or a weaker absorption may be understood in particular an absorption by a tissue in which one or more blood vessels are embedded. By a small and/or a smaller value of a pixel may be understood in particular a value from the value range, which value range is formed by the values of the pixels of the second image and/or of the contrast agent image which relate to one or more blood vessels filled with contrast agent and/or to a metal object. By a large and/or a larger value of a pixel may be understood in particular a value from the value range, which value range is formed by the values of the pixels of the first image and/or of the mask image which relate to a tissue in which one or more blood vessels are embedded.

An embodiment of the invention enables an improved image registration of the first image relative to the second image. In particular, an embodiment of the invention enables eggshell artifacts to be effectively suppressed and/or avoided.

An embodiment of the inventive transformation determination device is embodied for determining a transformation for image registration of a first image relative to a second image and has a test series ascertainment module, a minimum test value determination module and a transformation determination module. The test series ascertainment module is embodied for ascertaining a test series of test elements, wherein each test element comprises a test transformation and a test value. The test series ascertainment module is embodied for performing at least the following for each test element of the test series:

ascertaining the test transformation of the test element based on a predetermined sequence of test transformations and/or based on one or more previously ascertained test elements, transforming the first image via the ascertained test transformation, ascertaining a difference image based on the transformed first image and the second image, and ascertaining the test value of the test element based on the difference image in such a way that the test value is a measure for an extension of a frequency distribution of values of pixels of the difference image in the direction in which the values of the pixels increase.

The minimum test value determination module is embodied for determining a minimum test value based on the test values encompassed by the test elements of the test series. The transformation determination module is embodied for determining the transformation which is the test transformation of a test element comprising the minimum test value.

According to an aspect of an embodiment of the invention, the inventive transformation determination device is embodied for performing an embodiment of the inventive method for determining a transformation for image registration. In particular, the ascertainment of the test series of test elements via the test series ascertainment module, the determining of the minimum test value via the minimum test value determination module and the determining of the transformation which is the test transformation of a test element comprising the minimum test value can be performed via the transformation determination module.

The image determination device according to an embodiment of the invention is embodied for determining a subtraction angiography image based on an original image pair set containing one or more original image pairs, wherein each original image pair of the original image pair set has a mask image and a contrast agent image. An embodiment of the inventive image determination device has an original image pair set provider module, a registered image pair ascertainment module and an image determination module.

The original image pair set provider module is embodied for providing the original image pair set. The registered image pair ascertainment module has an embodiment of the inventive transformation determination device and a transformation module. The registered image pair ascertainment module is embodied for ascertaining a registered image pair set containing one or more registered image pairs by performing at least the following for each original image pair of the original image pair set:

determining a transformation by way of an embodiment of the inventive transformation determination device, wherein the first image is the mask image of the original image pair and the second image is the contrast agent image of the original image pair, and transforming the mask image by way of the determined transformation via the transformation module, wherein the transformed mask image and the contrast agent image form a registered image pair of the registered image pair set.

The image determination module is embodied for determining the subtraction angiography image based on the registered image pair set.

According to an aspect of an embodiment of the invention, an embodiment of the inventive image determination device is embodied for performing an embodiment of the inventive method for determining a subtraction angiography image. In particular, the providing of the original image pair set via the original image pair set provider module, the ascertaining of a registered image pair set via the registered image pair ascertainment module, the determining of a transformation for image registration via the transformation determination device, the transforming of the mask image via the transformation module, and the determining of the subtraction angiography image based on the registered image pair set can be performed via the image determination module.

An embodiment of an inventive determination device is to be understood as a device that is chosen from the group including an embodiment of an inventive transformation determination device and an embodiment of an inventive image determination device. An embodiment of the inventive imaging apparatus includes an embodiment of the inventive determination device.

An embodiment variant of the invention provides that the imaging apparatus is a medical imaging apparatus and/or that the imaging apparatus has a raw data acquisition apparatus and/or a patient support apparatus. The raw data acquisition apparatus is embodied for acquiring a raw data set. In particular, the raw data acquisition apparatus can comprise a radiation source and a detector. In a C-arm X-ray machine, the radiation source can be an X-ray source and the detector an X-ray detector. In a magnetic resonance tomography system, the radiation source can be a radiofrequency antenna and the detector the same radiofrequency antenna or a further radiofrequency antenna. The patient support apparatus is embodied for supporting and positioning a patient.

An embodiment variant of the invention provides that the imaging apparatus has a control device and an image reconstruction device. The control device can be a computer, for example. In particular, the inventive determination device can be embodied as part of a control device of an imaging apparatus. The image reconstruction device is embodied for ascertaining a first image and a second image, in particular a mask image and a contrast agent image, of a region to be imaged of an object examined via the imaging apparatus based on a raw data set, e.g. using a reconstruction method.

An embodiment variant of the invention provides that an embodiment of the inventive determination device and/or one or more components of the inventive determination device are realized at least in part in the form of software on a processor system. In particular, the test series ascertainment module, the minimum test value determination module, the transformation determination module, the original image pair set provider module, the registered image pair ascertainment module, the transformation module and the image determination module in each case form a component of an embodiment of the inventive determination device. An embodiment variant of the invention provides that an embodiment of the inventive determination device and/or one or more components of an embodiment of the inventive determination device are realized at least in part in the form of software-assisted hardware, for example FPGAs or the like.

An embodiment variant of the invention provides that the original image pair set is provided with the aid of a data transfer from the original image pair set provider module to the registered image pair ascertainment module. An embodiment variant of the invention provides that the original image pair set provider module has at least one access module for accessing a memory area, e.g. of a computer and/or control device of an imaging apparatus, in which the original image pair set is stored. The data transfer can be accomplished e.g. by way of a suitable interface. An embodiment variant of the invention provides that interfaces for data transfer to and/or from components of the inventive determination device are realized at least in part in the form of software. In particular, the interfaces can have at least one access module for accessing suitable memory areas in which data can be suitably buffered, retrieved and updated. The interfaces can also be embodied as hardware-based interfaces which are controlled via suitable software.

A largely software-based implementation has the advantage that existing control devices already used in the prior art can also be easily upgraded via a software update in order to operate in the inventive manner. In this respect an embodiment relates to a corresponding computer program product having a computer program which can be loaded into a memory device of a computer, wherein an embodiment of an inventive method is performed by way of the computer program when the computer program is executed in the control device. As well as the computer program, such a computer program product can comprise additional software components, e.g. documentation, and/or hardware components, e.g. a hardware key (dongle, etc.) to enable use of the software.

In an embodiment, in order to transport the computer program to the control device and/or to store the computer program on or in the control device, a computer-readable medium can be used, for example a memory stick, a hard disk or some other transportable or permanently installed data medium on which a computer program which can be loaded into a memory device of a computer is stored, wherein an embodiment of an inventive method is performed by way of the computer program when the computer program is executed on the computer. An embodiment variant of the invention provides that the control device has a processor system. The processor system can be formed e.g. by one or more cooperating microprocessors.

According to an aspect of an embodiment of the invention, the imaging apparatus is chosen from the group including a C-arm X-ray machine, a computed tomography device, a single photon emission computed tomography device (SPECT device), a positron emission tomography device (PET device), a magnetic resonance tomography device, and combinations thereof. In particular, the imaging apparatus can comprise an X-ray machine, an ultrasound device and similar. The imaging apparatus can furthermore be a combination of a plurality of imaging and/or irradiation modalities. In this case an irradiation modality can comprise for example an irradiation device for radiation therapy.

Within the scope of the invention, features which are described in relation to different embodiment variants and/or different claims categories (method, device, etc.) can be combined to form further embodiment variants. In particular, the features, advantages and embodiment variants described in relation to the inventive method can also be applied to the inventive determination device, the inventive imaging apparatus, the inventive computer program product, and the inventive computer-readable medium, and vice versa. In other words, the object-related claims can also be developed on the basis of the features which are described or claimed in connection with a method. Functional features of an inventive method can in this case be implemented by correspondingly embodied components or modules of the inventive transformation determination device and/or of the inventive image determination device. The use of the indefinite articles "a" or "an" does not preclude the possibility that a plurality of the features in question may also be present.

The described method, the described transformation determination device, the described image determination device and the described imaging apparatus are simply embodiment variants of the invention. The invention can be varied by the person skilled in the art without leaving the scope of the invention insofar as this is defined by the claims.

FIG. 1 shows a flowchart of a method for determining a transformation for image registration of a first image relative to a second image according to a first embodiment variant of the invention. At step DTR, a test series of test elements is ascertained, wherein each test element comprises a test transformation and a test value. Each test element of the test series is ascertained by performing steps TT, T1, DI and TV in each case. At step TT, the test transformation of the test element is ascertained based on a predetermined sequence of test transformations and/or based on one or more previously ascertained test elements. At step T1, the first image I1 is transformed via the ascertained test transformation. At step DI, a difference image is ascertained based on the transformed first image TI1 and the second image I2. At step TV, the test value of the test element is ascertained based on the difference image in such a way that the test value is a measure for an extension of a frequency distribution of values of pixels of the difference image in the direction in which the values of the pixels increase. At step MIN, a minimum test value is determined based on the test values encompassed by the test elements of the test series. At step DT1, the transformation which is the test transformation of a test element comprising the minimum test value is determined.

Figure 2:
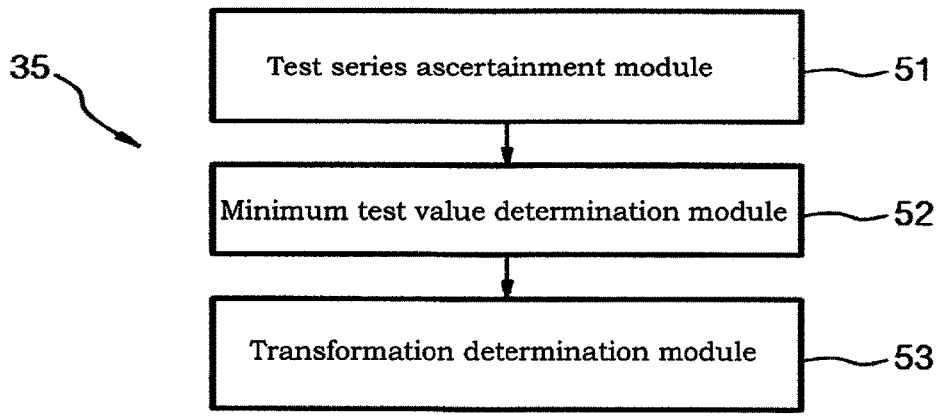
FIG. 2 is an illustration of a transformation determination device according to a second embodiment variant of the invention.

FIG. 2 shows an illustration of a transformation determination device 35 according to a second embodiment variant of the invention. The transformation determination device 35 is embodied for determining a transformation for image registration of a first image I1 relative to a second image I2 and has a test series ascertainment module 51, a minimum test value determination module 52 and a transformation determination module 53.

The transformation determination device 35 is embodied in particular for performing the method according to the first embodiment variant of the invention. In particular, the ascertaining DTR of the test series of test elements via the test series ascertainment module 51, the determining MIN of the minimum test value via the minimum test value determination module 52 and the determining DT1 of the transformation which is the test transformation of a test element comprising the minimum test value can be performed via the transformation determination module 53.

In the embodiment variants shown below, invention-developing features in particular are described with reference to the respective hereintofore-explained embodiment variants. Features, in particular steps and components, which remain substantially the same are labeled with the same reference signs.

FIG. 3 shows a flowchart of a method for determining a subtraction angiography image based on an original image pair set containing one or more original image pairs, wherein each original image pair of the original image pair set has a mask image and a contrast agent image, according to a third embodiment variant of the invention.

At step PI, the original image pair set is provided. At step RI, a registered image pair set containing one or more registered image pairs is ascertained by performing steps DT3 and T3 for each original image pair of the original image pair set. At step DT3, a transformation for image registration is determined by way of the method according to the first embodiment variant of the invention, wherein the first image is the mask image of the original image pair and the second image is the contrast agent image of the original image pair. At step T3, the mask image is transformed via the determined transformation, wherein the transformed mask image and the contrast agent image form a registered image pair of the registered image pair set. At step DS, the subtraction angiography image is determined based on the registered image pair set.

FIG. 4 shows an illustration of an image determination device 60 according to a fourth embodiment variant of the invention. The image determination device 60 is embodied for determining a subtraction angiography image based on an original image pair set containing one or more original image pairs, wherein each original image pair of the original image pair set has a mask image and a contrast agent image. The image determination device 60 has an original image pair set provider module 61, a registered image pair ascertainment module 62 and an image determination module 64. The registered image pair ascertainment module 62 has a transformation determination device 35 according to the second embodiment variant of the invention and a transformation module 63.

The image determination device 60 is embodied in particular for performing the method according to the third embodiment variant of the invention. In particular, the providing PI of the original image pair set via the original image pair set provider module 61, the ascertaining RI of a registered image pair set via the registered image pair ascertainment module 62, the determining DT3 of a transformation via the transformation determination device 35, the transforming T3 of the mask image via the transformation module 63, and the determining DS of the subtraction angiography image based on the registered image pair set can be performed via the image determination module 64.

Figure 5:
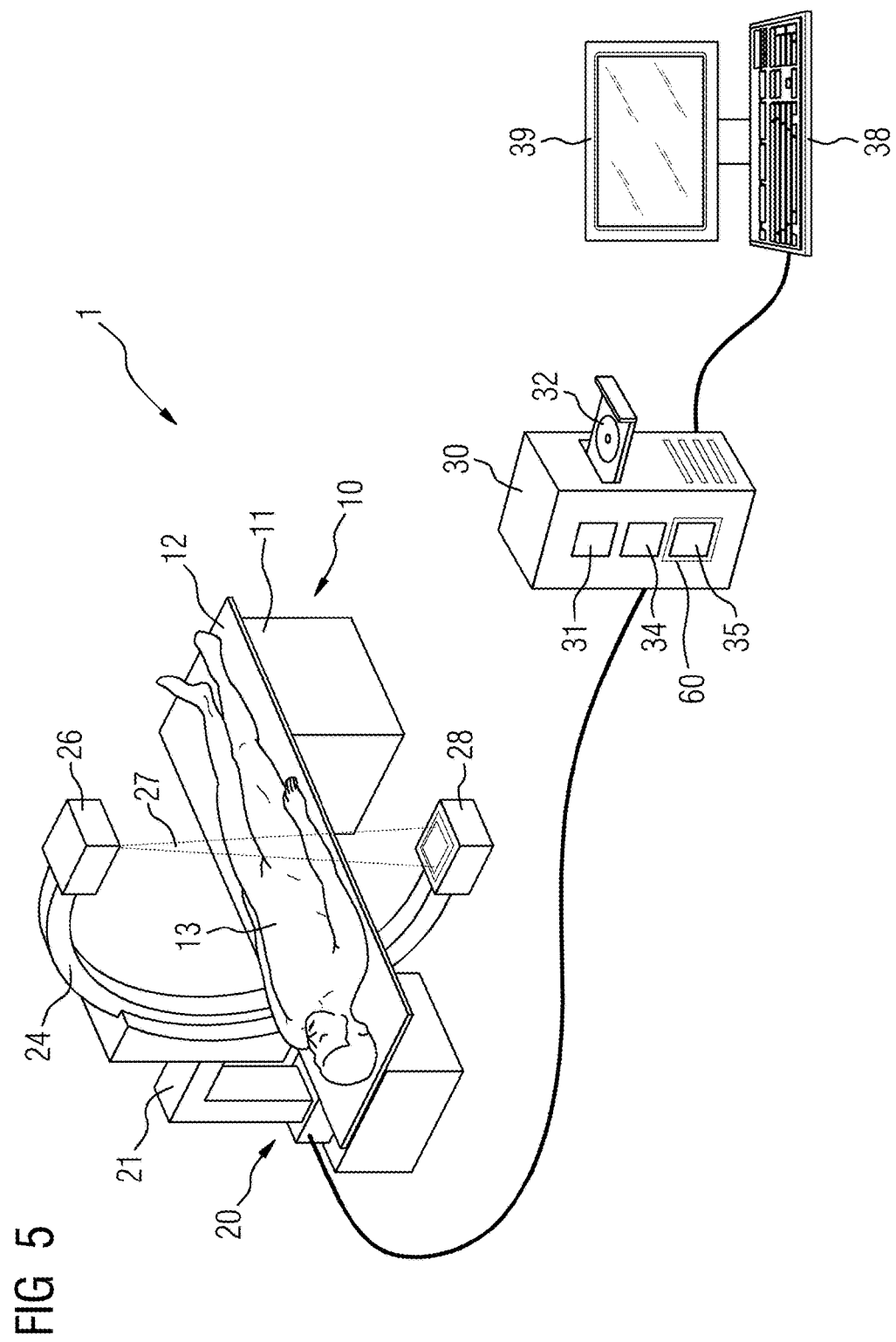
FIG. 5 is an illustration of an imaging apparatus according to a fifth embodiment variant of the invention.

FIG. 5 shows an imaging apparatus 1 according to a fifth embodiment variant of the invention. Without limitation of the general inventive concept, a C-arm X-ray machine 1 is shown by way of example for the imaging apparatus 1. The fifth embodiment variant of the invention provides that the raw data acquisition apparatus 26, 28 is a projection data acquisition apparatus 26, 28, that the raw data set is a projection dataset, that the radiation source 26 is an X-ray source 26, and that the detector 28 is an X-ray detector 28, in particular a flat-panel image detector.

The imaging apparatus 1 has a C-arm apparatus 20, a patient support apparatus 10 and a projection data acquisition apparatus 26, 28. The patient support apparatus 10 has a support table 11 and a support tabletop 12 for supporting and positioning the patient 13. The C-arm apparatus 20 has a stationary supporting frame 21 and a C-arm 24. The C-arm 24 is movable, in particular able to pivot, relative to the patient support apparatus 10. This enables different arrangements of the radiation source 26 and the detector 28 to be set relative to the region to be imaged of the patient 13.

The projection data acquisition apparatus 26, 28 is embodied for acquiring a projection dataset. The projection data acquisition apparatus 26, 28 has a radiation source 26 which is embodied for emitting radiation quanta 27 and a detector 28 which is embodied for detecting the radiation quanta 27. A region to be imaged of an object, in particular of the patient 13, can be arranged between the radiation source 26 and the detector 28. The radiation quanta 27 are able to travel from the radiation source 26 to the region to be imaged of the patient 13 and impinge on the detector 28 following an interaction with the region to be imaged. In this way a projection profile of the region to be imaged can be acquired. The projection profile can be in particular two-dimensional. Projection data acquired by the projection data acquisition apparatus 26, 28 is forwarded to the control device 30. The control device 30 is embodied in particular for acquiring, storing, retrieving, post-processing and providing the projection data in the form of a projection profile and/or in the form of a projection dataset. A projection dataset can comprise one or more projection profiles.

By moving the projection data acquisition apparatus 26, 28 relative to the patient support apparatus it is possible to acquire at least one projection profile in each case for different arrangements of the radiation source 26 and the detector 28 relative to the region to be imaged.

The first image and/or the mask image can be in particular a first projection profile and/or be ascertained based on a first projection dataset. In this case the first projection profile and/or the first projection dataset can relate to a mask examination status of the region to be imaged in which the region to be imaged has no contrast agent or contrast agent in a concentration that is not relevant for the contrast agent imaging.

The second image and/or the contrast agent image can be in particular a second projection profile and/or be ascertained based on a second projection dataset. In this case the second projection profile and/or the second projection dataset can relate to a contrast agent examination status of the region to be imaged in which the region to be imaged has a contrast agent, in particular in a concentration that is suitable for contrast agent imaging.

Optionally, the imaging apparatus 1 can have a contrast agent injection apparatus for injecting a contrast agent into the patient 13. A contrast agent injection can be e.g. at least partially automated with the aid of a contrast agent injection module of the control device 30 and/or be performed manually by an operator.

The imaging apparatus 1 has a control device 30, an input device 38 and an output device 39. The control device 30 is a computer, in particular a digital computer, and is embodied for controlling the imaging apparatus 1. The input device 38 is embodied for inputting control information, e.g. image reconstruction parameters and/or examination parameters. The output device 39 is embodied for outputting control information and/or images, in particular for outputting the subtraction angiography image. The control device 30 has a memory device 31. The memory device 31 is embodied for loading a computer program, in which case the steps of an inventive method are performed via the computer program when the computer program is executed on the control device 30.

The imaging apparatus 1 has an image reconstruction device 34, the transformation determination device 35 according to the second embodiment variant of the invention and the image determination device 60 according to the fourth embodiment variant of the invention. Both the image reconstruction device 34 and the image determination device 60 together with transformation determination device 35 are implemented in the form of software on a processor system of the control device 30.

Via the image reconstruction device 34, an image dataset can be ascertained based on a projection dataset. The image dataset can comprise e.g. the first image and/or the second image and/or one or more mask images and/or one or more contrast agent images and/or one or more original image pairs and/or an original image pair set. The image dataset can be stored in particular by the image reconstruction device 34 and/or by the control device 30 in a memory area of the control device 30.

FIG. 6 shows, in a greatly simplified illustration, a first image I1, a second image I2 and a transformed first image TI1 according to a sixth embodiment variant of the invention. The sixth embodiment variant of the invention provides that the values of the pixels of the first image I1 and the values of the pixels of the second image I2 are grayscale values. In FIG. 6, a brighter gray shade of a pixel corresponds to a larger value, in particular grayscale value, of the pixel. The first image I1 is a mask image. The second image I2 is a contrast agent image. On account of the contrast agent, the value of the pixels relating to the blood vessel BV is significantly smaller in the second image I2 than in the first image. The blood vessel BV is embedded in a tissue ST having a large grayscale value. The value of the pixel relating to a metal coil CA inserted into an aneurysm is particularly small. A misregistration of the first image I1 relative to the second image I2 is present. The consequence of the misregistration is in particular that in a pixel-by-pixel combination of the first image I1 and the second image I2, the pixel of the first image I1 relating to the metal coil CA inserted into an aneurysm is combined with a pixel of the second image I2 relating to the tissue ST. In particular, a difference image which is ascertained by pixel-by-pixel subtraction of the first image I1 from the second image I2 has a large value at the position at which the pixel relating to a metal coil CA inserted into an aneurysm is located in the first image I1. This value is approximately equal to the value of the pixels relating to the tissue ST.

The transformed first image TI1 has been produced from the first image via a transformation for image registration that was determined with the aid of a method according to the first embodiment variant of the invention. In a pixel-by-pixel combination of the transformed first image TI1 and the second image I2, the pixels of the second image I2 which relate to the tissue ST are combined with the pixels of the transformed first image TI1 which relate to the tissue ST. In particular, a difference image which is ascertained via a pixel-by-pixel subtraction of the transformed first image TI1 from the second image I2 does not have a large value at any position.

The fact that the contrast agent image comprises pixels which relate to a blood vessel BV filled with contrast agent and which therefore have small values does not have a disrupting effect on the method for determining the transformation for image registration according to the first embodiment variant of the invention, because the transformation is determined in such a way that large values of pixels in the difference image are avoided. In conventional methods for determining a transformation for 2D-2D image registration it can happen that pixels of the second image which relate to a blood vessel filled with contrast agent and pixels of the first image which relate to a metal object are registered onto one another and/or are combined with one another during the pixel-by-pixel combining of the transformed first image and the second image.

Advantages of embodiments of the invention taking clinical data as an example are explained with reference to FIGS. 7 to 10.

Figure 7:
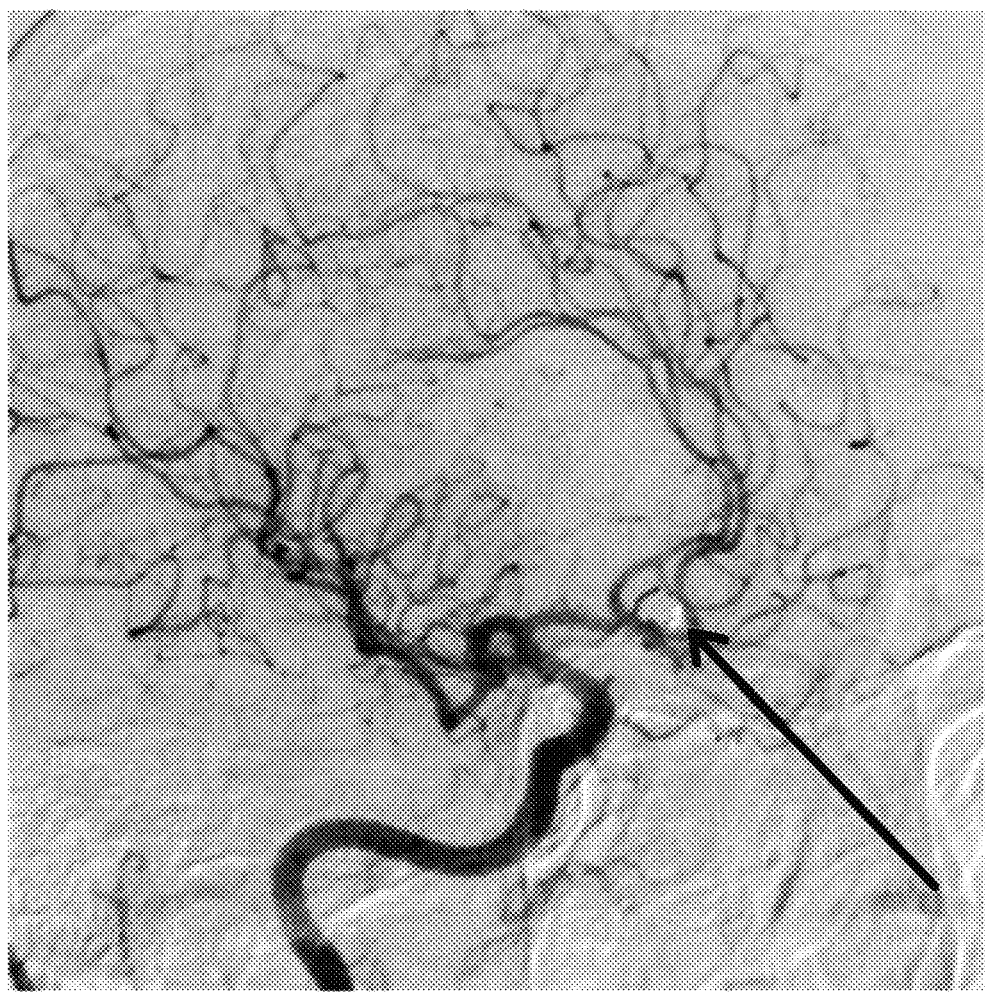
FIG. 7 shows a difference image which has been ascertained by pixel-by-pixel subtraction of a mask image from a contrast agent image.

FIG. 7 shows a difference image which has been ascertained by pixel-by-pixel subtraction of a mask image from a contrast agent image, wherein the mask image is misregistered relative to the contrast agent image. Contours of a metal coil which has been inserted into an aneurysm are clearly recognizable and are marked by an arrow.

Figure 8:
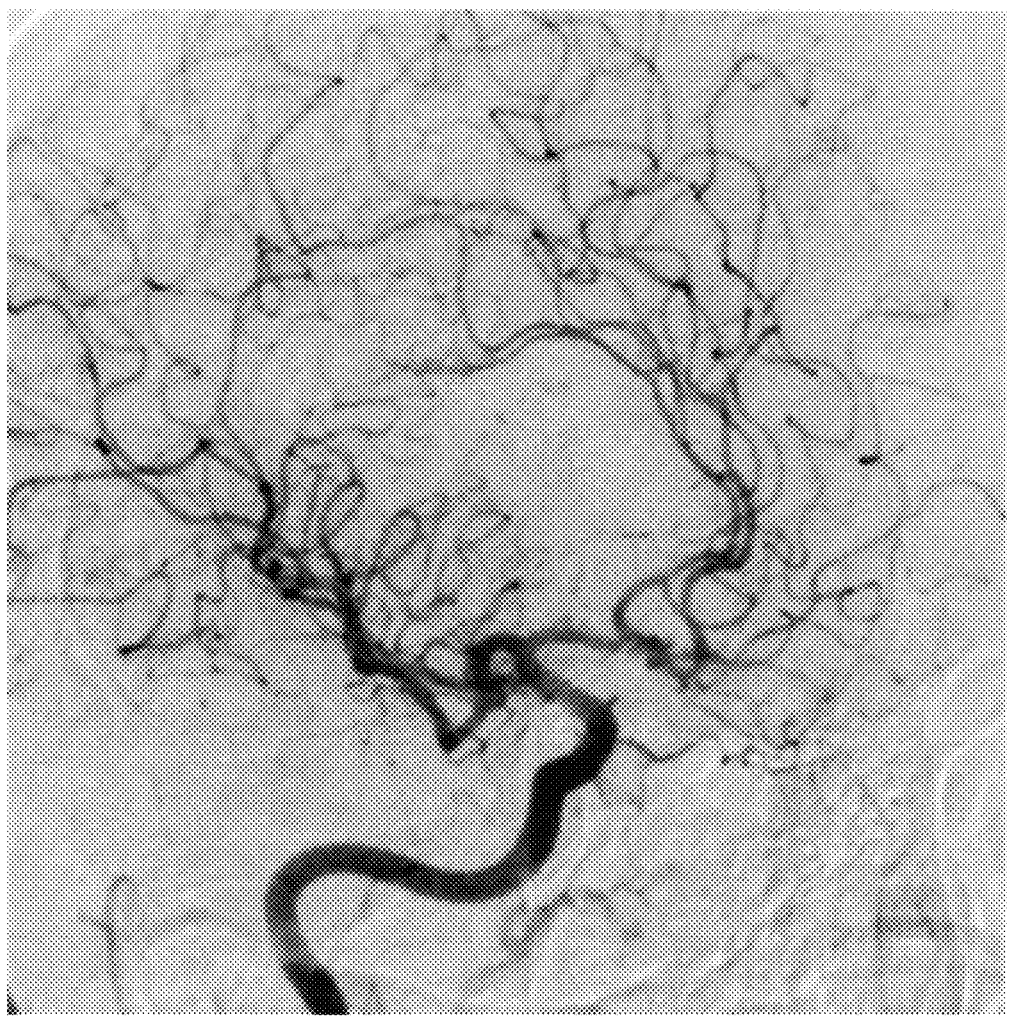
FIG. 8 shows a difference image which has been ascertained by pixel-by-pixel subtraction of a transformed mask image from a contrast agent image.

FIG. 8 shows a difference image which has been ascertained by pixel-by-pixel subtraction of a transformed mask image from a contrast agent image. In this case the mask image and the contrast agent image are the same as those on which the difference image shown in FIG. 7 is also based. The mask image has been transformed via a transformation that was determined with the aid of an inventive method for determining a transformation for image registration. The misregistration as well as the contours of the coil are avoided as a result.

Figure 9:
FIG. 9 shows a 3D subtraction angiography image which has been determined based on an original image pair set.

FIG. 9 shows a 3D subtraction angiography image (3D-DSA image) which has been determined based on an original image pair set. In this case the original image pair set has an original image pair comprising the mask image and the contrast agent image on which the difference image shown in FIG. 7 is based. On account of the misregistration of the mask image relative to the contrast agent image shown in FIG. 7, the 3D-DSA image has an artifact, in particular of a type known as an eggshell artifact. The arrow marks the aneurysm into which the coil has been inserted. On the basis of the 3D-DSA image shown in FIG. 9 the impression could be created that a blood flow is taking place into the aneurysm into which the coil has been inserted, which could result in a misdiagnosis.

Figure 10:
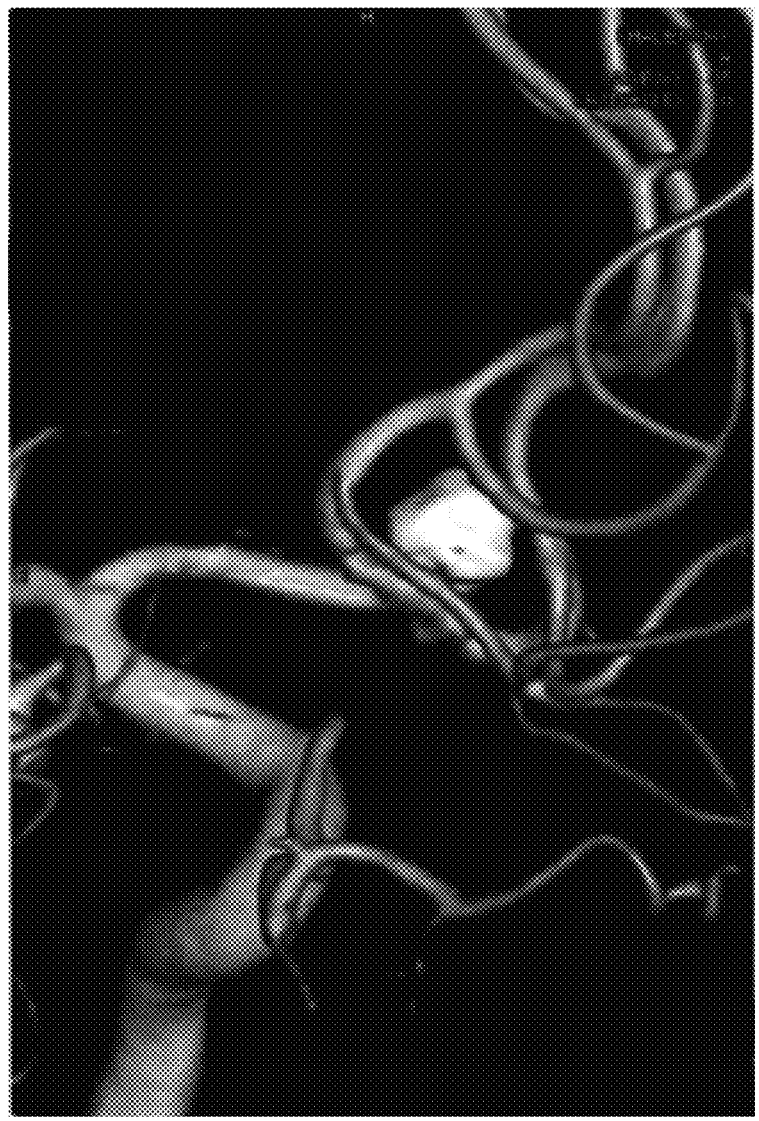
FIG. 10 shows a 3D subtraction angiography image which has been determined based on a registered image pair set.

FIG. 10 shows a 3D subtraction angiography image (3D-DSA image) which has been determined by way of an inventive method for determining a subtraction angiography image. The 3D-DSA image shown in FIG. 9 and the 3D-DSA image shown in FIG. 10 are based on the same original image pair set. In the determining of the 3D-DSA image shown in FIG. 10, the mask image for each original image pair of the original image pair set has been transformed by way of a transformation that was determined with the aid of an inventive method for determining a transformation for image registration. The eggshell artifact is avoided as a result.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a registration transformation for image registration of a first image relative to a second image, comprising:
    generating a plurality of test elements, each test element among the plurality of test elements including a test transformation and a test value, the generating including determining a test element among the plurality of test elements by at least
        determining a test transformation of the test element based on at least one of
            a sequence of test transformations, or
            one or more previously determined test elements among the plurality of test elements,
        transforming the first image via the determined test transformation,
        generating a difference image based on the transformed first image and the second image,
        calculating a frequency distribution of pixel values of the difference image, and
        determining a test value of the test element based on the frequency distribution such that the test value increases as one or more frequencies of higher pixel values increase;
    determining a minimum test value among the test values included in the plurality of test elements; and
    determining the registration transformation as the test transformation included in the same test element as the minimum test value.

2. The method of claim 1, wherein the test value is determined based on a pixel group of the difference image, each pixel of the pixel group meeting at least one of
    a pixel position condition relating to a position of the pixel, or
    a pixel value condition relating to a pixel value of the pixel.

3. The method of claim 2, wherein the test value is at least one of
    a parameter of at least one of the pixel group or the difference image, or
    determined based on a parameter of at least one of the pixel group or the difference image, and wherein
    the parameter includes at least one of a maximum of the pixel values, a sum of the pixel values or a location parameter of the frequency distribution.

4. The method of claim 3, wherein the location parameter includes at least one of a mean value, a mode or a quantile.

5. The method of claim 3, wherein the pixel position condition is met if the pixel is positioned in a region of interest.

6. The method of claim 3, wherein the pixel value condition is met if the pixel value exceeds a pixel threshold value.

7. The method of claim 2, wherein the pixel position condition is met if the pixel is positioned in a region of interest.

8. The method of claim 2, wherein the pixel value condition if the pixel value exceeds a pixel threshold value.

9. The method of claim 2, wherein the test transformation comprises at least one of a translation or a rotation.

10. The method of claim 2, wherein the test transformation is determined by way of a search algorithm.

11. The method of claim 2, further comprising:
    comparing the test value with a test threshold value; and
    discontinuing the determining a test element in response to determining that the test value is lower than the test threshold value based on the comparing.

12. A method for determining a subtraction angiography image based on a first image pair set containing one or more first image pairs, each of the one or more first image pairs including a mask image and a contrast agent image, the method comprising:
    providing the first image pair set;
    generating a registered image pair set containing one or more registered image pairs by performing at least the following for each of the one or more first image pairs of the first image pair set
        determining a registration transformation for image registration via the method of claim 2, the first image being the mask image of the first image pair and the second image being the contrast agent image of the first image pair, and
        transforming the mask image via the determined registration transformation, the transformed mask image and the contrast agent image forming a registered image pair of the registered image pair set; and
    determining the subtraction angiography image based on the registered image pair set.

13. The method of claim 1, wherein the test transformation comprises at least one of a translation or a rotation.

14. The method of claim 1, wherein the test transformation is determined by way of a search algorithm.

15. The method of claim 1, further comprising:
comparing the test value with a test threshold value; and
discontinuing the determining a test element in response to determining that the test value is lower than the test threshold value based on the comparing.

16. A method for determining a subtraction angiography image based on a first image pair set containing one or more first image pairs, each of the one or more first image pairs including a mask image and a contrast agent image, the method comprising:
providing the first image pair set;
generating a registered image pair set containing one or more registered image pairs by performing at least the following for each of the one or more first image pairs of the first image pair set
determining a registration transformation for image registration via the method of claim 1, the first image being the mask image of the first image pair and the second image being the contrast agent image of the first image pair, and
transforming the mask image via the determined registration transformation, the transformed mask image and the contrast agent image forming the registered image pair of the registered image pair set; and
determining the subtraction angiography image based on the registered image pair set.

17. A non-transitory computer-readable medium storing computer-readable instructions that, when executed by at least one processor, cause the at least one processor to perform the method of claim 16.

18. A non-transitory computer-readable medium storing computer-readable instructions that, when executed by at least one processor, cause the at least one processor to perform the method of claim 1.

19. The method of claim 1, further comprising:
identifying pixels of the difference image having a corresponding pixel value that exceeds a pixel value threshold,
wherein the calculating calculates the frequency distribution of pixel values of the identified pixels.

20. The method of claim 1, wherein
the frequency distribution includes a plurality of frequency bins, each frequency bin of the plurality of frequency bins being associated with a corresponding pixel value range of a plurality of different pixel value ranges, the plurality of frequency bins including a highest frequency bin associated with a highest pixel value range of the plurality of different pixel value ranges, the highest pixel value range including a highest pixel value of the pixel values of the difference image, and
the determining includes determining the test value based on the frequency distribution such that the test value increases as one or more frequencies of the highest frequency bin increase.

21. The method of claim 1, wherein the determining includes:
determining the test value based on the frequency distribution such that the test value increases as a highest pixel value of the pixel values of the difference image increases.

22. A transformation determination device for determining a registration transformation for image registration of a first image relative to a second image, comprising:

a first memory configured to store first computer-readable instructions thereon; and
at least one first processor coupled to the first memory and configured to execute the first computer-readable instructions to
generate a plurality of test elements, each test element among the plurality of test elements including a test transformation and a test value, the generation including determining a test element among the plurality of test elements by at least
determining a test transformation of the test element based on at least one of
a sequence of test transformations, or
one or more previously determined test elements among the test plurality of test elements,
transforming the first image via the determined test transformation,
generating a difference image based on the transformed first image and the second image,
calculating a frequency distribution of pixel values of the difference image, and
determining a test value of the test element based on the frequency distribution such that the test value increases as one or more frequencies of higher pixel values increase,
determine a minimum test value among the test values included in the plurality of test elements, and
determine the registration transformation as the test transformation included in the same test element as the minimum test value.

23. An image determination device comprising:
the transformation determination device of claim 22.

24. An image determination device for determining a subtraction angiography image based on a first image pair set containing one or more first image pairs, each of the one or more first image pairs including a mask image and a contrast agent image, the image determination device comprising the transformation determination device of claim 22, wherein the at least one first processor is further configured to execute the first computer-readable instructions to
provide the first image pair set;
generate a registered image pair set containing one or more registered image pairs by performing at least the following for each of the one or more first image pairs of the first image pair set
determining a registration transformation via the transformation determination device, the first image being the mask image of the first image pair and the second image being the contrast agent image of the first image pair, and
transforming the mask image via the determined registration transformation, the transformed mask image and the contrast agent image forming a registered image pair of the registered image pair set; and
determine the subtraction angiography image based on the registered image pair set.

25. An imaging apparatus comprising:
the image determination device of claim 24.

26. An image determination device for determining a subtraction angiography image based on a first image pair set containing one or more first image pairs, each of the one or more first image pairs including a mask image and a contrast agent image, the image determination device comprising:
a second memory configured to store second computer-readable instructions thereon; and at least one second processor coupled to the second memory and configured to execute the second computer-readable instructions to provide the first image pair set, generate a registered image pair set containing one or more registered image pairs by performing at least the following for each of the one or more first image pairs of the first image pair set determining a registration transformation via the transformation determination device of claim 22, the first image being the mask image of the first image pair and the second image being the contrast agent image of the first image pair, and transforming the mask image via the determined registration transformation, the transformed mask image and the contrast agent image forming a registered image pair of the registered image pair set, and determine the subtraction angiography image based on the registered image pair set.

27. An imaging apparatus comprising:
the transformation determination device of claim 22.

28. The method of claim 1, wherein
the test value is determined based on a pixel group of the difference image,
the test value is at least one of
a parameter of at least one of the pixel group or the difference image, or
determined based on the parameter of at least one of the pixel group or the difference image, and
the parameter includes at least one of a maximum of the pixel values, a sum of the pixel values or a location parameter of the frequency distribution.

29. The method of claim 28, wherein the location parameter includes at least one of a mean value, a mode or a quantile.

\* \* \* \* \*